United States Patent
Efobi

(10) Patent No.: US 9,615,974 B1
(45) Date of Patent: Apr. 11, 2017

(54) WOUND CARE PAD MANAGEMENT SYSTEM AND DEVICE

(71) Applicant: Pius Efobi, Long Branch, NJ (US)

(72) Inventor: Pius Efobi, Long Branch, NJ (US)

(*) Notice: Subject to any disclaimer, the term of this patent is extended or adjusted under 35 U.S.C. 154(b) by 557 days.

(21) Appl. No.: 14/051,587

(22) Filed: Oct. 11, 2013

Related U.S. Application Data

(60) Provisional application No. 61/712,992, filed on Oct. 12, 2012.

(51) Int. Cl.
*A61F 13/00* (2006.01)

(52) U.S. Cl.
CPC .. *A61F 13/00085* (2013.01); *A61F 13/00072* (2013.01)

(58) Field of Classification Search
CPC .................................................. A61F 13/00085
USPC ........................... 128/893–894; 206/440–441
See application file for complete search history.

(56) References Cited

U.S. PATENT DOCUMENTS

| | | | |
|---|---|---|---|
| 2,579,403 A * | 12/1951 | Slomowitz | A61F 13/0203 128/888 |
| 4,374,520 A | 2/1983 | Grossmann et al. | |
| 4,545,371 A | 10/1985 | Grossmann et al. | |
| 4,863,424 A * | 9/1989 | Blake, III | A61M 25/1027 604/103 |
| 6,436,432 B2 | 8/2002 | Heinecke et al. | |
| 6,508,430 B1 * | 1/2003 | Rodriguez | A61F 15/005 242/546.1 |
| 8,252,970 B2 * | 8/2012 | Buckman | A61B 17/1325 424/443 |
| 2008/0171068 A1 * | 7/2008 | Wyner | A01N 25/10 424/404 |
| 2010/0044491 A1 * | 2/2010 | Ritchey | A61F 15/005 242/422.4 |
| 2011/0257574 A1 | 10/2011 | Svensby | |

OTHER PUBLICATIONS

CN2115933 Arden, Russi USA—Feb. 18, 1994 application for canadian Patent.*

* cited by examiner

*Primary Examiner* — Tarla Patel
(74) *Attorney, Agent, or Firm* — Harpman & Harpman

(57) ABSTRACT

A system for wound management to maintain wound dressing isolation from the caregiver. The system includes a flexible wound pad with exterior separated wound engagement fields and a self-engaging applicator isolation pad retainment placement removal handle element which can be selectively used by the caregiver to manipulate the wound pad on the patient.

5 Claims, 3 Drawing Sheets

WOUND CARE PAD MANAGEMENT SYSTEM AND DEVICE

This application claims the benefit of U.S. Provisional Application No. 61/712,992, filed Oct. 12, 2012.

BACKGROUND OF THE INVENTION

1. Technical Field

This invention relates to wound care cleaning and removal of dressing applied to the wound.

2. Description of Prior Art

Prior art wound management dressings; cleaning and removal have been developed to provide a sterile environment for the treatment of wounds. Such devices and systems can be seen, for example, in U.S. Pat. Nos. 4,374,520, 4,545,371, 6,436,432 and U.S. Patent Publication 2011/0257574 A1.

In U.S. Pat. Nos. 4,374,520 and 4,545,371 systems and methods for bandaging a patient are disclosed wherein a large adhesive back bandage is applied having an application handle on oppositely disposed sides thereof.

U.S. Pat. No. 6,436,432 isolates an absorbent sterile pad dressing from a delivery system having a carrier frame overlapping a heavy absorbent wound pad defining a window from which in the pad is accessible.

U.S. Patent Publication 2011/0257574 discloses a device to facilitate the application of plastic film to skin of a patient as a component in a wound dressing sterile application field format.

There are also a number of different prior art wound care kits that include a variety of selected supplies to efficiently clean and measure a wound with a sterile solution, multiple gauze pads of specific size and redressing of the wound with wet or dry dressing gauze sequence and overlying large pressure pad that is secured by tape or other well defined methods.

Such prior art wound care kits rely on specific caregiver sequence procedures to maintain a sterile wound field which includes gloves, given the direct contact needed to remove, clean, assess and redress the wound by the caregiver.

SUMMARY OF THE INVENTION

An integrated sterile wound pad and applicator system for the treatment of open wounds wherein a sterile field must be maintained and proper wound cleaning methodology should be observed. The wound pad has dual oppositely disposed sterile gauze surfaces of varying depths, as required, separated by a non-porous flexible support carrier sheet therebetween. A self-engaging applicator pad engagement and applicator assures that there is no direct contact with the wound pad by the caregiver as it is manipulated on the wound and removed by spiral rotation about the applicator engaging and collecting the pad within itself on the applicator without direct contact by the caregiver.

DETAILED DESCRIPTION OF THE INVENTION

Figure 1:
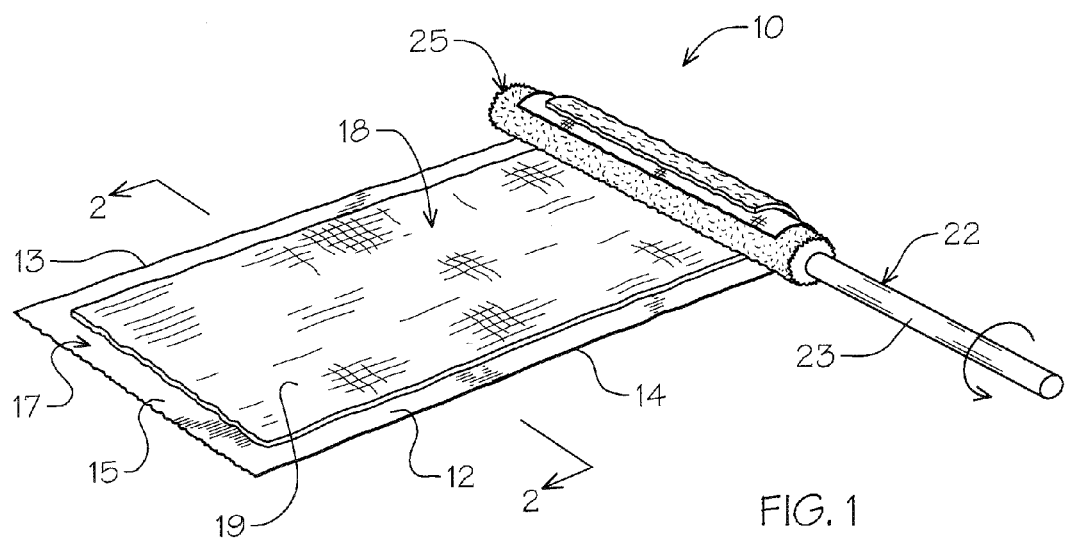
FIG. 1 is a perspective view of the wound pad and applicator partially engaged thereon.
Figure 2:
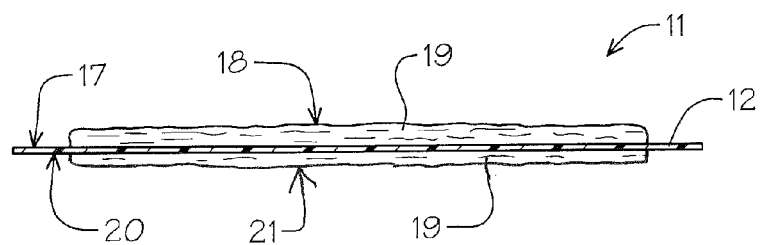
FIG. 2 is an enlarged cross-sectional view of the wound pad of the invention.
Figure 3:
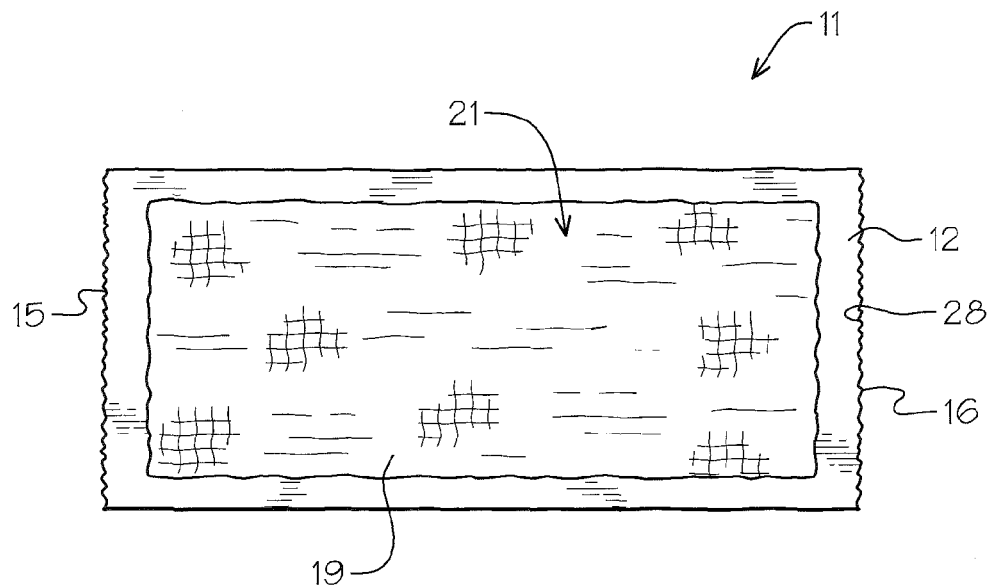
FIG. 3 is a top plan view of the wound pad illustrating the associated gauze surface field within the support carrier sheet.

Referring now to FIGS. 1, 2 and 3 of the drawings, a wound pad system 10 of the invention can be seen having a wound pad 11 with a generally rectangular exterior shape chosen for illustration purposes only. It is noted that other dimensional shapes may be used including, but not limited to square, ovaloid and round dependent on the nature of the wound and criteria to be addressed.

The wound pad 11 has a main carrier sheet 12 of a flexible non-porous material of a uniform thickness and density. The carrier sheet 12 has oppositely disposed spaced parallel side edges 13 and 14 and corresponding interlinking respective spaced parallel end edges 15 and 16 therebetween.

An upper mounting surface 17 on the carrier sheet 12 has a fixed first usable surface covering 18 formed of multiple layers of inter-joined gauze material 19 defining a sterile absorbent field of a known density acceptable for use in medical environments as is understood within the art.

An oppositely disposed lower mounting surface 20 of the flexible carrier sheet 12 has a fixed second usable surface covering 21 also formed of multiple layers of inter-joined gauze material 19 defining a corresponding sterile absorbent field of a known density for use in medical environments, specifically in wound cleaning care and dressing, as best seen in FIG. 2 of the drawings. It will be noted that the respective gauze coverings 18 and 21 are of different relative dimensional height and are spaced inwardly of the respective perimeter sides 13 and 14 and interengaged end edges 15 and 16 of the hereinbefore described carrier sheet 12 to maintain a supporting field carrier within the confines thereof as seen in FIG. 3 of the drawings.

Figure 4:
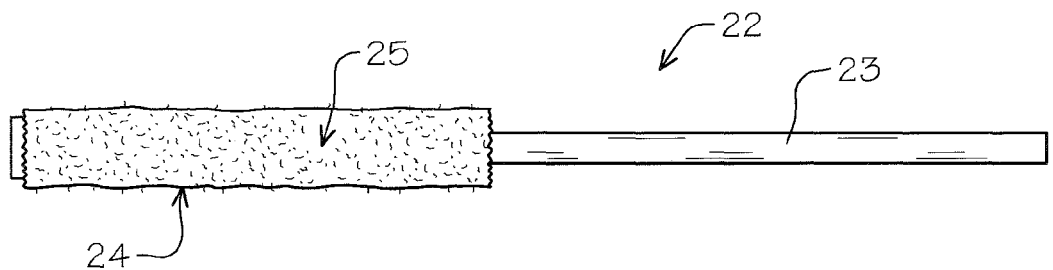
FIG. 4 is a side elevational view of the isolation applicator device.

Referring now to FIGS. 1 and 4 of the drawings, a wound care applicator 22 can be seen having a handle portion 23 and a pad engagement portion 24. The handle portion 22 is of an elongated rod-like configuration have a terminal distal end 23A and may be formed preferably of a non-porous molded material, such as synthetic resin.

The pad engagement portion 24 is defined as having an enlarged cylindrical surface 25 of an increased diameter having a pad engagement retainment surface covering such as a plurality of engagement hooks derived from the well known hook and loop engagement and release material known under the brand name Velcro, for example. It will also be noted that a variety of other texturing elements can be applied to the pad engagement portion 24 as a covering for selective engagement and retainment of the gauze surface of the wound pad 11, as hereinbefore described.

It will be evident additionally that as seen in FIG. 1 of the drawings, that the applicator 22 is used to selectively engage and hold onto the corresponding effacing gauze surfaces 18 or 19 for manual manipulation of the wound pad 12 over the surface of a wound, not shown, and for removal thereof as will be described in detail hereinafter.

In use, by selectively engaging the wound pad 10 with the application 22, pad engagement portion 24 the "hook" enabled surface 25 thereof will interlock with the gauze covering 18, as shown. By rotation of the integral handle portion 23, the wound pad 11 can be rolled up thereon thereby isolating the opposing contaminated gauze surface 21, in this example, within the coiling action of the upper first gauze surface 18 assuring complete isolation of the wound pad surface from contact with the caregiver (not shown) who is manipulating the applicator's extended handle portion 22, as hereinbefore described.

Figure 5:
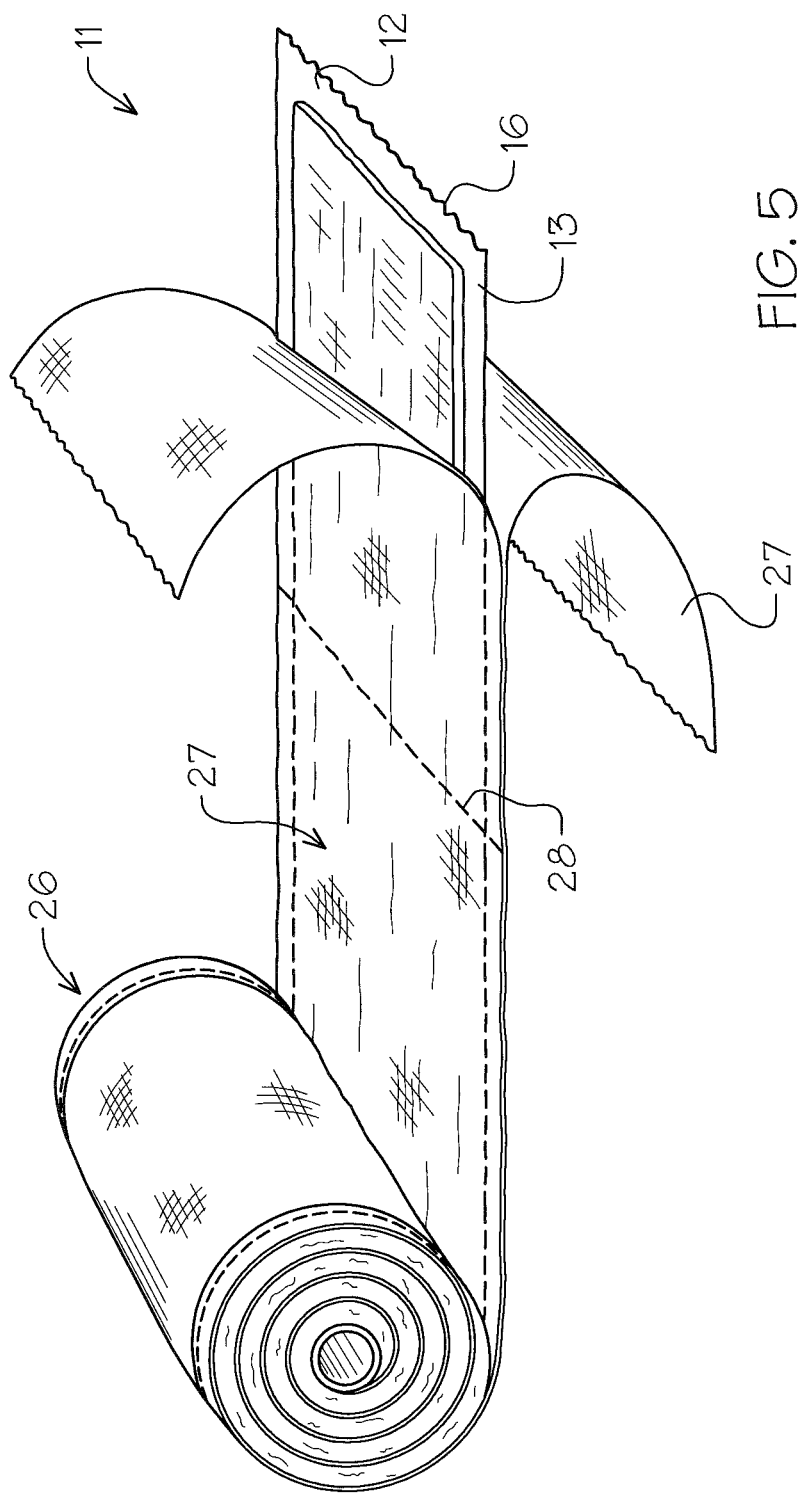
FIG. 5 is a perspective view of a plurality of wound pads within sterile dispensing packaging for ease of use within the venue.

Referring now to FIG. 5 of the drawings, a storage dispensing wound pad arrangement packaging is illustrated which shows an example of how a plurality of such wound pads 11 of the invention could be, but not required to be stored and dispensed.

In this illustration, a roll 26 of individual sealed wound pads 11 is formed by a continuous strip of packaged pods, having a sterile maintaining paper release cover 27 so that individual wound pads 11 can be sequentially separated at the perforation line 28 in the packaging between each of pads 11. The perforation tear line 28 would extend through the sterile packaging covering 27 and correspondingly separate the carrier sheet 12 so that a selected wound pad could be easily removed for use as illustrated graphically by the separation of the sterile cover sheet 27 affording access and usability to the dual surface wound pad 11 of the invention.

It will thus be seen that a new and novel dual sided wound pad 11 of the invention and its associated applicator engagement manipulator and removal device has been illustrated and disclosed and that various changes and modifications may be made therein without departing from the spirit of the invention.

Therefore I claim:

1. A system for wound care and bandaging a patient comprising in combination, a flexible dual sided wound pad and a wound pad applicator, said wound pad having a first sterile pad surface and a second sterile pad surface, a flexible carrier sheet between said respective first and second sterile pad surfaces for supporting and maintaining said sterile pads in aligned opposing relation to one another, said wound pad applicator having a cylindrical elongated wound pad engagement portion and a handle portion, said wound pad engagement portion having a textured elongated annular surface of increased annular dimension to that of said handle portion, said textured elongated annular surface having a plurality of individual flexible fabric hooks engaged on said first sterile pad surface for application and removal of said wound pad by rolling up said wound pad on said wound pad applicator.

2. The system for wound care set forth in claim 1 wherein said first and second sterile pad surfaces are formed from multiple layers of gauze material.

3. The system for wound care set forth in claim 1 wherein said first and second sterile pad surfaces are of different relative dimensional height to one another.

4. The system for wound care set forth in claim 1 wherein said carrier sheet of a known surface dimension greater than that of said first and second sterile pad surfaces positioned respectively thereon.

5. The system for wound care set forth in claim 1 wherein said textured surface of increased annular dimension is pre-attached to said wound pad engagement portion of said wound pad applicator.

\* \* \* \* \*